United States Patent [19]
Lindkvist

[11] Patent Number: 5,345,928
[45] Date of Patent: Sep. 13, 1994

[54] SYSTEM ARRANGEMENT FOR THE EVACUATION OF ANAESTHESIA OR ANALGESIA GAS

[75] Inventor: Allan Lindkvist, Umeå, Sweden

[73] Assignees: Medicvent AB, Umeå, Sweden; Berner International GmbH, Elmshorn, Fed. Rep. of Germany

[21] Appl. No.: 910,035
[22] PCT Filed: Feb. 6, 1991
[86] PCT No.: PCT/SE91/00082
§ 371 Date: Aug. 6, 1992
§ 102(e) Date: Aug. 6, 1992
[87] PCT Pub. No.: WO91/12043
PCT Pub. Date: Aug. 22, 1991

[30] Foreign Application Priority Data

Feb. 7, 1990 [SE] Sweden .............. 9000445

[51] Int. Cl.$^5$ .............................. A61M 15/00
[52] U.S. Cl. ................. 128/203.12; 128/205.12; 128/205.19; 128/910
[58] Field of Search ............ 128/203.12, 205.12, 128/205.19, 910

[56] References Cited

U.S. PATENT DOCUMENTS

| | | | |
|---|---|---|---|
| 4,219,020 | 8/1980 | Czajka | 128/207.13 |
| 4,265,239 | 5/1981 | Fischer, Jr. | 128/205.17 |
| 4,770,169 | 9/1988 | Schmoegner | 128/207.13 |

FOREIGN PATENT DOCUMENTS

WO82/01999 6/1982 Sweden.

*Primary Examiner*—Edgar S. Burr
*Assistant Examiner*—Aaron J. Lewis
*Attorney, Agent, or Firm*—Jacobson, Price, Holman & Stern

[57] ABSTRACT

A system for collecting and removing leaking anesthesia or analgesia gas from an anesthesia apparatus in an operation theater or the like includes a vacuum source (1) and an anesthesia mask (5) adapted to be placed onto the face of a patient and connected to the anesthesia apparatus by at least one supply and removing device, through which the patient is supplied with a mixture of anesthesia or analgesia gas and air and through which air-gas mixture exhaled by the patient is removed, and a vacuum line (4) connected to the anesthesia mask for removing leaking gas to the vacuum source. A T-shaped joint (10) is connected in the vacuum line (4) and has one opening connected by a branch line (11) to the supply and removing device for removing exhaled gas-air mixture via the vacuum source. A noise damping or reducing device (18) is arranged in the vacuum line to reduce disturbing noise as far as possible. A flow regulator device (19, 20, 21) is provided for controlling the evacuation capacity according to the demand in order to reduce both noise and cooling effect.

19 Claims, 2 Drawing Sheets

SYSTEM ARRANGEMENT FOR THE EVACUATION OF ANAESTHESIA OR ANALGESIA GAS

This invention relates to an anesthesia system for safeguarding of the necessary suction or evacuation effect and function at plants or systems where there is a demand for evacuation simultaneously with utilizing so called double masks or the like.

BACKGROUND OF THE INVENTION

In arranging evacuation plants or systems for the evacuation of leaked out or otherwise free anesthesia or analgesia gases it is naturally very important to design and dimension the suction devices in an appropriate way. At the same time it is urgent and important to adjust the capacity of the suction sources in such a way that the suction force remains at the desired value. The Swedish patent No 8008962-6 and European patent No. EP 0 067 196 disclose a known anesthesia mask, equipped with means for evacuation of leaked out gas and the mask is so designed that it catches or collects and evacuates gas leaking out between the mask edge and the face of the patient, but is also so arranged that it is able to catch and evacuate all gas streaming out from the mask as the mask is removed from the face of the patient and is held free. For this purpose the mask proper is equipped with a circumferential slot or opening connected to a suction source. Behind the invention lies a number of problem which now have found a solution, viz.

evacuation also of gases exhaled by the patient noise generation at the device adaption of the capacity to different sizes of anesthesia masks.

With modern anesthesia arrangements there are besides the means for supplying of anesthesia gas also an evacuation system, which is adapted to remove the exhaled gas mixed with air directly from the mask. Thus, to the mask there are connected both a gas supply main and an evacuation main and furthermore the suction pipe or tube connected to the slot evacuation arrangement of the mask according to the above patents. It is of utmost importance that the vacuum inside the evacuation main is maintained at such a level that the respiratory system of the patient in no way will be affected and this is the reason why there are built in safety devices preventing the vacuum from adversely affecting the patient. The capacity of the evacuation system is normally of a range 20–30 liters per hour. With systems of the type described and including so called double mask devices principally no gas at all or very little gas will leak out in the operation theater.

A known apparatus discloses a control valve having a input opening for so called fresh gas, i.e. the intended mixture of anesthesia gas and oxygen/air and to this input opening a compensation ballon is connected to an open branch pipe, which ballon in sequence with the breathing of the patient will be emptied and filled again. The evacuation line for exhaled air is also arranged at the control valve and via an open branch line connected with a so called reservoir, i.e. a flexible tank or container open towards the atmoshpere, also serving as a balancing or compensation means but having as its main purpose to prevent a vacuum build up beyond the allowed limits in the evacuation main if the pipe or tube to the mask would be partially blocked.

Many hospitals and clinics, however, have no permanent systems for the supply of anesthesia gas and the evacuation of exhaled air, but utilize portable anesthesia apparatuses and gas bottles. With such apparatuses the exhalation normally is done directly into the operation theatre via a check valve arranged at the mask, which naturally results in a severe contamination of the air in the operating theatre and necessiatates a powerful general ventilation thereof. The use of masks of the type mentioned earlier herein and securing an evacuation of leaked out gas along the edge of the mask and capturing gas from the mask when lifted, naturally partially improves the situation, but is in no way sufficient as the exhaled air with its high anesthesia gas contents escapes freely into the operation theatre atmosphere.

Even if systems and plants arranged for the use of so called double masks work highly satisfactorily both technically and functionally there is an irritating thing which is regarded as disturbing, viz. the sound, or rather noise, generated by the evacuation. There even exist a certain, although small, risk in that the staff—in order to get rid of the noise—under certain circumstances will reduce the suction capacity alternatively and turn off the apparatus alltogether.

Another possible point of irritation is the cooling effect occuring when an airstream passes the hands, for example, of a person staying close to the place of evacuation and also the cooling effect occuring when holding a hose or a pipe, through which air or gas streams. It is furthermore desirable to keep both free gas and air streams and streams inside pipes and tubes at the lowest possible velocity level.

Decisive for a proper function of the system according to the European and Swedish patents is, as already mentioned, the ability of suction, but for the overall performance not only the suction ability is of importance. If that were the case one could restrict the system to just as large a ventilator or fan device as possible.

The suction ability may be too low. Then it is unable to attract the streams of gas which just pass by. The suction ability also can be to powerful, and bias the intended flow of anesthesia gases and in difficult cases also have an inpact on the respiration of the patient. To this may be added the cooling effect created when an air stream passes the facial skin or the like and such draft caused by the suction means is highly unpleasant when felt. The velocity or volume of the sucked in air also is of significance with regard to the sound generation. On low velocity the sound will be hardly noticeable, but as soon as the velocity increases, the sound will increase.

The volume of supplied fresh gas and volume of exhaled air respectively naturally vary with the the patients. A small child does not need as large a volume of fresh gas and does not exhale as large volumes as a grown person. It would be desirable to not only supply fresh gas to but also evacuate and remove gas from the patient in question in the same way as different types and sizes of masks are used depending on the patient.

BRIEF SUMMARY OF THE INVENTION

One object of this invention is to bring about an arrangement adaptable to different needs, making it possible to remove in the most efficient way all gas both exhaled and leaked out at the mask or otherwise escaped with a minimum of noise, cooling effect and other gas movement disturbing effects.

An additional object of the invention is to provide a device enabling evacuation of the exhaled air without the need for specific evacuation systems.

Still another object is to provide an arrangement which in an effective way reduces the noise unavoidably created by evacuation systems to which operators and personel are exposed and which is regarded as disturbing their concentration.

In order to enable an adaption of the suction force to the type of mask, e.g. masks for children and masks for grownups, there exists a need for controlling the suction force. The alternative would be—in order to have the required suction force available all the time—to utilize maximum suction force, both from a technical point of view and in consideration of the creation of undesired noise. A further object, thus, is to make such controlling and adaption possible.

The above objects are achieved by the instant invention which provides a system for removing leaked out or escaping anesthesia or analgesia gas from an anesthesia apparatus in an operation theater including a vacuum source and an anesthesia mask adapted to be positioned onto the face of a patient and connected to the anesthesia apparatus by at least one channel device through which the patient is supplied with a mixture of anesthesia or analgesia and air through which air gas mixture exhaled by the patient is removed. The mask has collecting means which are connected to the vacuum source through a vacuum line to remove anesthesia or analgesia gas, the vacuum line having therein a T-shaped joint containing an ejector device therein connected to the vacuum line and connected to the expired gas-air mixture removing means by a branch line to remove and forward the expired gas-air mixture to the vacuum source. The ejector device produces a vacuum in the branch line differing from the vacuum in the vacuum line. A noise damping or reducing means is arranged in the removal of evacuation channel to reduce disturbing noise and includes a casing having an effective flow area significantly larger than that of the vacuum line. A device is also provided for controlling the evacuation capacity according to the demand in order to reduce both noise and cooling effect.

BRIEF DESCRIPTION OF THE DRAWINGS

The invention will now be described in detail with reference to the accompanying drawings wherein.

DETAILED DESCRIPTION

Figure 1:
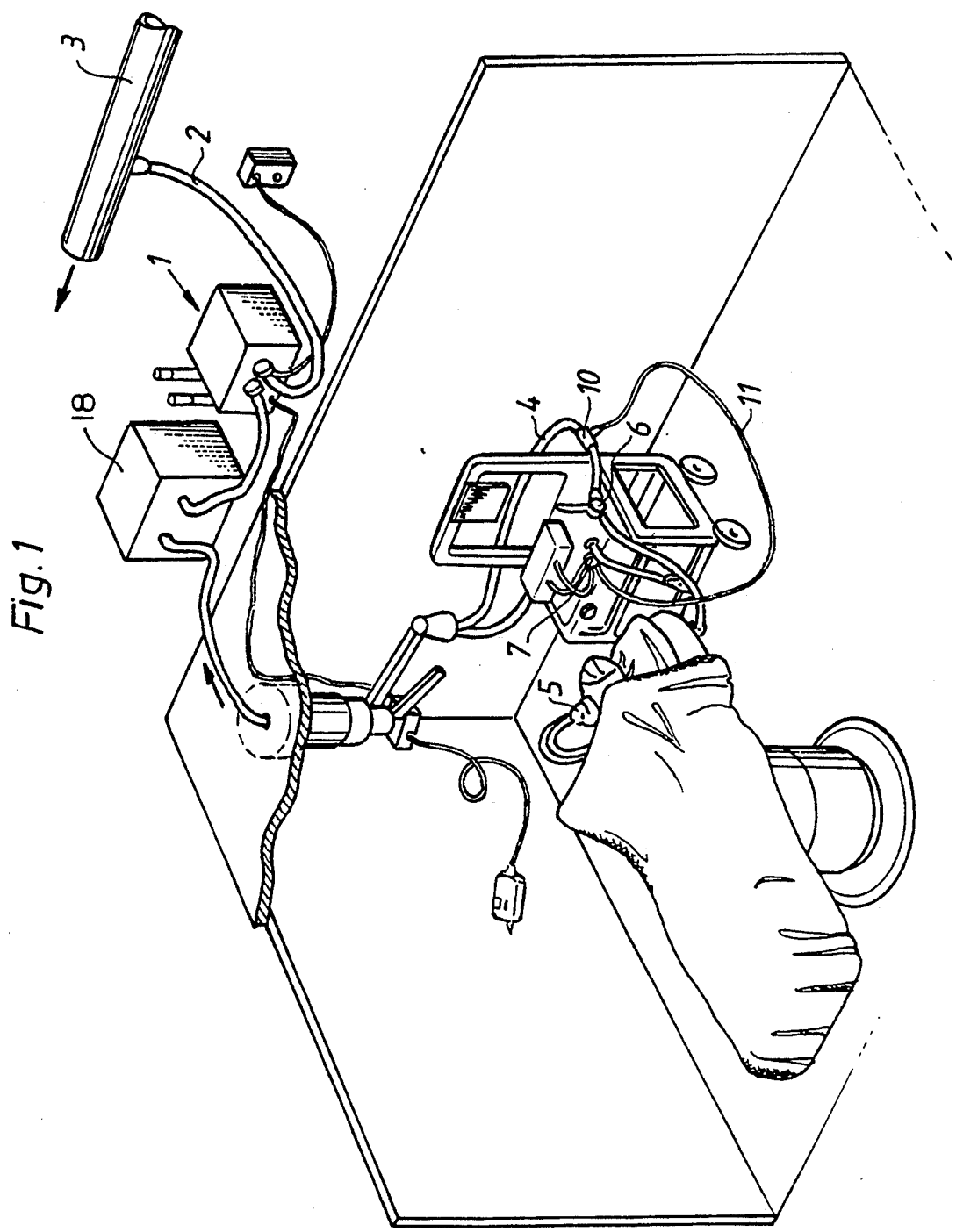
FIG. 1 is a perspective view schematically illustrating an evacuation system according to the invention.

In the system, to which the arrangement according to this invention is adapted to be connected, is included a vacuum source in the form of a fan unit 1, which via an exhaust hose 2 is connectable to a permanent evacuation duct means 3 of a building alternatively in a room, e.g. an evacuation flue or valve for the general ventilation.

To the fan unit there is also connected a tube arrangement or suction channel 4, connected to an anesthetic mask 5 via an intermediary section varying according to the type of anesthetic system. The suction channel normally has a safety valve and flow meter 6 and also a resonance or damping chamber to be described later.

The mask 5 is supplied anesthetic gas via a control and dosage unit generally designated 7 connected to an anesthetic gas source by a pressure and volume controller connected to the mask.

There are two main types of such control and dosage units, viz. the so called D system and the Circle system.

Figure 4:
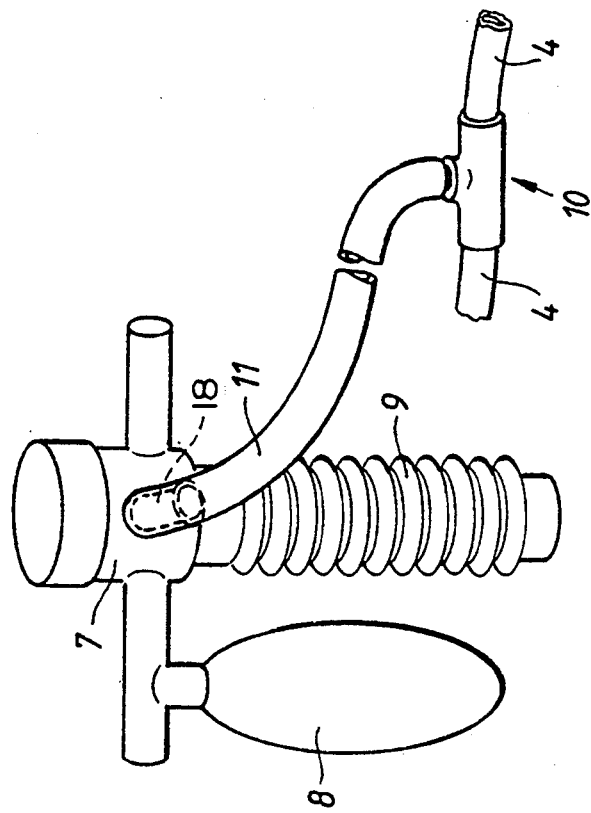
FIG. 4 is an enlarged perspective view the connections at a control valve.

In order to clarify this there is shown in FIG. 4 an apparatus, i.e. a control and dosage unit 7 equipped with a so called breathing bubble or balloon 8 portioning out the fresh gas and also indicating if the breathing takes place in a normal way, and a so called reservoir 9 formed by a downwardly open pleated hose. The reservoir serves as a compensating vessel on the evacuation and secures that the pulsing exhalation may take place in the intended way in spite of the fact that the evacuation is essentially continuous. The reservoir is downwardly open also in order to be able to serve as a safety valve if a fault occurs between the reservoir and the mask so that no vacuum build up can take place. When—via a tube 11 connected to an evacuation joint 11a—all exhaled air is removed, no vacuum build up can occur in the mask or within the respiratory system of the patient—the latter certainly resulting in grave danger—and pressure compensation will occur by air entering the reservoir 9 from below.

The control of the evacuation may also take place by means of a valve sensing the breathing sequence or the like means opening and closing the evacuation in pace with the inhalation and exhalation respectively.

The known masks 5 with evacuation of excess and leaked out gas have the ability to prevent anesthetic gas from streaming out into the environment both when the mask is kept applied towards the face of the patient and when held free, but they are not adapted or intended to take care of all exhaled air. Such air or part thereof will be removed and evacuated at so called Circle systems in the way earlier mentioned. And in this case there is arranged for such evacuation in the operation theater.

In order to enable removal and evacuation of exhaled air also in places devoid of means for evacuation there is, according to this invention arranged at the suction tube 4 between the mask 5 and the fan unit 1, a suction connection 10, which—as shown in FIG. 4—via a branch pipe or hose 11 is connectable to an evacuation joint 11a on conventional control valve 7.

Figure 2:
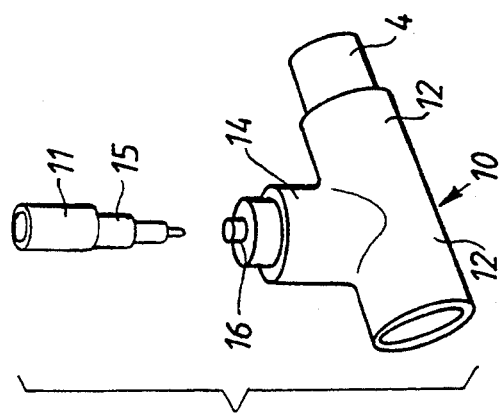
FIG. 2, is perspective view showing one connecting unit with attached tube nipple.
Figure 3:
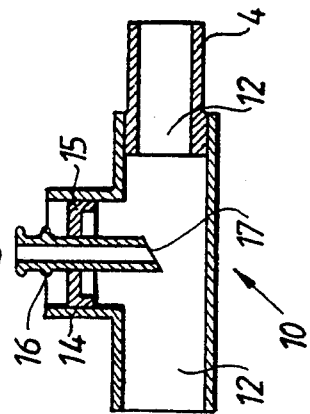
FIG. 3 is a cross-sectional view of the connecting unit of FIG. 2.

The connection proper 10 shown in FIGS. 2 and 3, includes a T-pipe with aligned connections 12 to which the suction tube 4 between the mask 5 and the fan unit 1 is connected. At the third connection 14 there is a washer means 15 through which extends a nipple or nozzle means 16, the inner end of which 17 is obliquely cut and extends essentially to the center axis of the straight passage 12—12 through the T-pipe. The. size or area of the nipple 16 is adapted to the existing or expected vacuum inside the suction line 4. This vacuum is controlled by the fan unit 1 and by a counter pressure or resistance means, normally constituted by the catching and removing parts of the mask 5 for leaked out or otherwise escaped gas, but may also be a separate adapted resistance body such as an end plug insertable into the end of the tube 11. By size adaption of the nipple 16 and adjusting the vacuum inside the pipe 4, the desired evacuation or suction capacity may be created inside the evacuation tube 11. By changing the nipple and/or adjusting for a change in vacuum inside the channel 4, different evacuation capacities may be had if necessary.

Through the evacuation joint 11a on control and dosage unit 7, connected to the evacuation tube 11 adapted thereto, anesthesia gas mixed with exhaled air may be removed also with systems devoid of per se known pressurized air driven ejector means or the like means. This results in an improvement of the environments and situation inside also spartan surgical rooms so that it will be fully comparable with operation theaters having central evacuation and at costs considerably lower than before.

It should here be noted that the noise production caused by the extra suction connection is negligible especially when compared with pressurized air driven ejectors which can have a very high noise level.

The evacuation capacity of the suction line 4 from the anesthetic mask 5 to the fan unit 1 in a high-flow-low-pressure system of the kind herein described is or ought to be in the range of 250–650 l/min, preferebly 580 l/min for large masks and from 280 to 440 l/min for medium to small masks. The capacity with the extra evacuation connection may be definitely lower and be in the range of 20–40 l/min, preferebly below 30 l/min.

The heavy reduction of capacity in the evacuation or branch lines 11a, is possibly due to the pressure drop arising at the connector device 10 and due to resisting pressure caused at the input end of the channel, i.e. the gas collecting means of the mask 5 and the reduced area at the nipple means 16. The reduction of suction capacity of course is biassed also by the difference between the areas of the suction pipe 4 and the nipple 16.

Since the suction velocity applies generally for the intended purposes one should keep within the limits given above, i.e. at about 250–650 l/min for the anesthetic mask suction. The capacity at the extra connection serving for the evacuation of the exhaled air may—as can be seen—be considerably lower and be in the range of 20–40 l/min.

Concerning the noise created inside the system it has been established that it is not only within the mask itself nor in its slot system, connections and the like where noise is created but also sharp corners and edges passed by high velocity air streams may result in so called standing waves. A considerable portion of the noise is created by the fan means 1.

Even if the fan per se is manufactured and designed to give a minimum of noise and has carefully ground surfaces and edges and polished channels, there occurs among other things because of purely mechanical sounds from the motor, sounds from bearings, other sounds such as alternating current hum and sounds within the control electronics and the oscillation or air columns a buzzing sound, which appears to arise from the mask, but in reality arises from the fan unit and the channel system. This sound or noise is surprisingly able to travel against the direction of the sucked in air.

According to the invention it is suggested to arrange in the suction tube or channel, at least between the fan unit 1 and the mask 5 means which may be regarded and functions as a resonance or damping chamber 18, and which includes a closed vessel with couplings for the tube 4 and perhaps an inside covering of sound or resonance damping material. In the preferred embodiment the two ends of the suction tube are coupled to the same end of the damping chamber so that the gas/air stream is forced to turn about inside the chamber.

By the resonance or damping chamber 18, the tendency for creation of noise producing standing waves within the tube system mostly by the fan, motor and control system sounds damped or absorbed are reduced.

Figure 5:
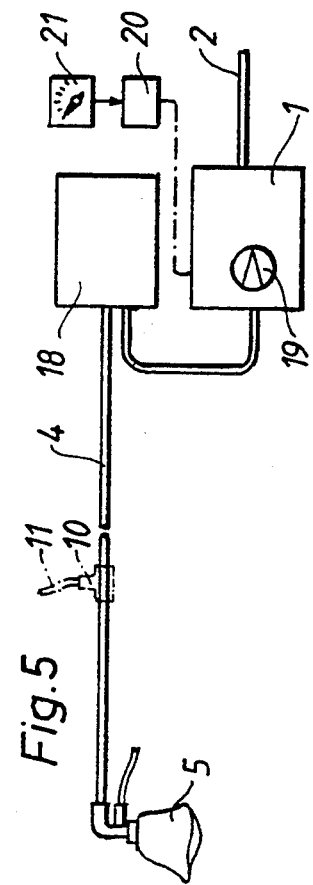
FIG. 5 is a schematic view showing an alternative embodiment of the system for reduction of the noise created by the evacuation device.

FIG. 5 illustrates how within the tube 4 between the fan unit 1 and the mask 5 a resonance chamber or box 18 has been connected, the chamber or box having a much larger cross sectional area than the tube 3 and which will force the air/gas stream to change its direction of movement.

By dividing the suction tube or hose 4 into two parts separated by the resonance damping box 18 a major part of the sound from the fan area towards the mask area will be eliminated. The resonance or damping chamber forming box may besides having an inside covering be completely empty and will—unlike other known silencer means having baffles and the like—in no detectable way influence or retard the gas/air streaming therethrough. The damper box, however, ought to be tight so that no leaking in air can enter and disturb the evacuation function at the mask.

A reduction of sound of more than 50% is fully possible by the arrangments mentioned above. The basic idea behind the sound damping means is to establish a widening along the tubes or hoses resulting in the breaking of standing waves occuring in channels, wherein also the length relation ratio between the tube parts on either side of the box and also the length of the chamber or box is influential and that inside the chamber sound damping material such as mineral wool may be applied, such material functioning so that the sound waves will be extinguished.

In order to keep the suction capacity within pre set limits and adapt it to the mask size utilized, there is arranged at the fan unit creating the necessary vacuum a speed control device. The speed of the fan motor is controlled by means of an electronic control unit 19, preferably built as an integrated circuit and with an automatically electronically controlled setable and vacuum sensing check or speed control device 20 and a manually operated switch device 21 for the setting of different effect steps and rotational speed areas.

In the preferred embodiment the control and setting device 20, 21 is arranged for more than two, preferably six steps, one for each mask size or mask size group, wherein the mask size, i.e. indirectly the size of the patient, is determined. As the suction velocity and capacity will influence the creation of noise and also the cooling effect, it is of importance that in each instance only the air velocity necessary for the intended function is utilized and not an unnecessary high velocity.

I claim:

1. A system for collecting and removing anesthesia from an anesthesia device in operation theaters comprising:
    an anesthesia gas source;
    a vacuum source;
    a mask device adapted to be applied to the face of a patient and having collecting means for collecting and removing anesthesia gas leaking out and escaping during operation of said system;
    at least one supply and removing means communicating said anesthesia gas source and air to said mask device for supplying a mixture of said anesthesia gas and air to said patient and for removing anesthesia gas and air mixture exhaled by said patient;
    a vacuum line connected between said vacuum source and said collecting means on said mask device for conducting said anesthesia gas collected by said collecting means to said vacuum source;

a T-shaped joint in said vacuum line having two aligned openings connected to said vacuum line so that a flow path is produced between said aligned openings;

a third opening in said T-shaped joint;

a branch line connecting said third opening to said at least one supply and removing means for conducting therefrom exhaled gas-air mixture to said T-shaped joint and said vacuum source; and ejector means in said third opening of said T-shaped joint for producing a vacuum in said branch line differing from said vacuum in said vacuum line.

2. The system as claimed in claim 1 wherein:
said ejector means comprises a throttling means in said T-shaped joint communicating said branch line with said vacuum line.

3. The system as claimed in claim 1 wherein:
said ejector means comprises an tubular nozzle affixed to said third opening of said T-shaped joint and having an obliquely cut inner end projecting into said flow path between said first and second openings in said T-shaped joint.

4. The system as claimed in claim 3 wherein:
said aligned openings in said T-shaped joint have a common central axis; and
said inner end of said nozzle extends substantially to said central axis.

5. The system as claimed in claim 1 and further comprising:
an upstream end on said vacuum line connected to said mask device; and
throttling means attached to said upstream end of said vacuum line.

6. The system as claimed in claim 5 and further comprising:
a control device connected to said branch line for limiting the volume capacity of said branch line to a given value.

7. The system as claimed in claim 5 wherein:
said throttling means comprises said collecting means of said mask device.

8. The system as claimed in claim 1 and further comprising:
a box shaped air-tight casing having an inlet and an outlet connected in said vacuum line between said collecting means of said mask device and said vacuum source so that said leaking and escaping anesthesia collected by said collecting means flows through said air-tight casing, said air-tight casing having an effective flow area significantly larger than the effective flow area of said vacuum line for damping noise in said system.

9. The system as claimed in claim 8 wherein:
said vacuum source comprises a fan unit;
said T-shaped joint is between said mask device and said air-tight casing; and
said air-tight casing is between said T-shaped joint and said fan unit.

10. The system as claimed in claim 9 wherein:
said flow regulator is operatively connected to said fan unit for controlling the speed of said fan unit.

11. The system as claimed in claim 8 wherein:
said inlet and outlet of said air-tight casing are offset with respect to each other.

12. The system as claimed in claim 11 wherein:
said inlet and outlet are disposed at the same side of said air-tight casing.

13. The system as claimed in claim 8 and further comprising:
a volumetric flow regulator in said vacuum line for controlling the volumetric flow in said vacuum line;
a set of masks comprising a plurality of masks each having a different size adapted to the size of a respective patient; and
switch means operatively connected to said flow regulator and adapted to be switched to different positions corresponding to said different mask sizes for adapting said volumetric flow to said different mask sizes.

14. The system as claimed in claim 13 wherein:
said aligned openings in said T-shaped joint have a common central axis; and
said inner end of said nozzle extends substantially to said central axis.

15. The system as claimed in claim 14 wherein:
said vacuum source comprises a fan unit; and
said flow regulator is operatively connected to said fan unit for controlling the speed of said fan unit.

16. The system as claimed in claim 14 wherein;
said vacuum source comprises a fan unit;
said T-shaped joint is between said mask device and said air-tight casing; and
said air-tight casing is between said T-shaped joint and said fan unit.

17. The system as claimed in claim 1 and further comprising:
a volumetric flow regulator in said vacuum line for controlling the volumetric flow in said vacuum line;
a set of masks comprising a plurality of masks each having a different size adapted to the size of a respective patient; and
switch means operatively connected to said flow regulator and adapted to be switched to different positions corresponding to said different mask sizes for adapting said volumetric flow to said different mask sizes.

18. The system as claimed in claim 17 wherein:
said volumetric flow regulator has minimum flow positions, maximum flow positions, and intermediary flow positions between said minimum and maximum flow positions, for controlling the volumetric flow in said vacuum line, said different positions of said switch means comprise one extreme position corresponding to said minimum flow, another extreme position corresponding to said maximum flow, and intermediate positions between said extreme positions corresponding to said intermediary flows.

19. The system as claimed in claim 17 wherein:
said vacuum source comprises a fan unit; and
said flow regulator is operatively connected to said fan unit for controlling the speed of said fan unit.

* * * * *